(12) United States Patent
Guzman et al.

(10) Patent No.: US 8,691,801 B2
(45) Date of Patent: *Apr. 8, 2014

(54) USE OF MANZAMINE COMPOUNDS IN ANTI-CANCER THERAPEUTIC REGIMENS

(75) Inventors: Esther A. Guzman, Fort Pierce, FL (US); Jacob D. Johnson, Silver Spring, MD (US); Amy E. Wright, Fort Pierce, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/550,880

(22) Filed: Jul. 17, 2012

(65) Prior Publication Data

US 2012/0289533 A1 Nov. 15, 2012

Related U.S. Application Data

(63) Continuation of application No. 11/708,767, filed on Feb. 20, 2007, now Pat. No. 8,232,266.

(60) Provisional application No. 60/775,435, filed on Feb. 22, 2006.

(51) Int. Cl.
| | | |
|---|---|---|
| *A01N 43/00* | (2006.01) | |
| *A61K 31/33* | (2006.01) | |
| *A01N 43/42* | (2006.01) | |
| *A61K 31/44* | (2006.01) | |

(52) U.S. Cl.
USPC .......................................... 514/183; 514/284

(58) Field of Classification Search
USPC ................................................. 514/183, 284
See application file for complete search history.

(56) References Cited

U.S. PATENT DOCUMENTS

| | | | | |
|---|---|---|---|---|
| 4,895,852 | A * | 1/1990 | Higa et al. | 514/281 |
| 4,895,853 | A * | 1/1990 | Higa et al. | 514/281 |
| 4,895,854 | A * | 1/1990 | Higa et al. | 514/281 |
| 6,720,331 | B2 * | 4/2004 | Yeh et al. | 514/292 |
| 2004/0019029 | A1 | 1/2004 | Hamann et al. | |
| 2005/0085554 | A1 | 4/2005 | Hamann et al. | |

OTHER PUBLICATIONS

Bergenfeldt, M. and Albertsson, M. "Current State of Adjuvant Therapy in Resected Pancreatic Adenocarcinoma" *Acta Oncologica*, 2006, vol. 45, pp. 124-135.

Boucher, M.J. et al., "MEK/ERK Signaling Pathway Regulates the Expression of Bcl-2, Bcl-$X_L$, and Mcl-1 and Promotes Survival of Human Pancreatic Cancer Cells," *J. Cell Biochem.*, 2000, vol. 79, pp. 355-369.

Fujioka, S. et al., "Function of Nuclear factor $_KB$ in Pancreatic Cancer Metastasis," *Clin. Cancer Res.*, Jan. 2003, vol. 9, pp. 346-354.

Gura, T. "Cancer Models: Systems for Identifying New Drugs are often Faulty" *Science*, Nov. 7, 1997, vol. 278, No. 5340, pp. 1041-1042.

Johnson, Ji et al. "Relationships between Drug Activity in NCI Preclinical in vitro and in vivo Models and Early Clinical Trials" *British Journal of Cancer*, 2001, vol. 84, No. 10, pp. 1424-1431.

Mahalingam, D. and Giles, F. "Challenges in Developing Targeted Therapy for Pancreatic Adenocarcinoma" *Expert Opin. Ther. Targets*, 2008, vol. 12, No. 11, pp. 1389-1401.

Motomura, W. et al., "Involvement of MEK-ERK Signaling Pathway in the Inhibition of Cell Growth by Troglitazone in Human Pancreatic Cancer Cells," *Biochem. Biophys. Res. Commun.*, 2005, vol. 332, pp. 89-94.

Tan, X. et al., "Involvement of the Mitogen-Activated Protein Kinase Kinase 2 in the Induction of Cell Dissociation in Pancreatic Cancer," *Int. J. Oncol.*, 2004, vol. 24, pp. 65-73.

Toyonaga, T. et al., "Blockade of Constitutively Activated Janus Kinase/Signal Transducer and Activator of Transcription-3 Pathway Inhibits Growth of Human Pancreatic Cancer," *Cancer Lett.*, 2003, vol. 201, pp. 107-116.

Van Laethem, J.L. and Marechal, R. "Emerging Drugs for the Treatment of Pancreatic Cancer," 2007, *Expert Opin. Emerging Drugs*, 2007, vol. 12, No. 2, pp. 301-311.

\* cited by examiner

*Primary Examiner* — Marcos Sznaidman
(74) *Attorney, Agent, or Firm* — Saliwanchik, Lloyd & Eisenschenk

(57) ABSTRACT

Manzamine compounds have been discovered to decrease cell dissociation and cell migration associated with the metastatic potential of cancer cells and a restoration of cancer cell susceptibility to agents, such as TRAIL, which can induce apoptosis. Specifically, Manzamine A has a formerly unrecognized utility in both blocking tumor cell invasion and tumor metastasis as well in restoring cancer cell susceptibility to standard chemotherapeutic agents which induce apoptosis and, therefore, has utility in treating cancer.

1 Claim, 2 Drawing Sheets

USE OF MANZAMINE COMPOUNDS IN ANTI-CANCER THERAPEUTIC REGIMENS

CROSS-REFERENCE TO A RELATED APPLICATION

This application is a continuation application of Ser. No. 11/708,767, filed Feb. 20, 2007; which claims the benefit of U.S. provisional application Ser. No. 60/775,435, filed Feb. 22, 2006, both of which are incorporated herein by reference in their entirety.

GOVERNMENT SUPPORT

The subject matter of this application has been supported in part by U.S. Government Support under National Institutes of Health Grant No. RO1 CA 093455. Accordingly, the U.S. Government has certain rights in this invention.

BACKGROUND OF INVENTION

Pancreatic cancer is the fourth leading cause of cancer death in the United States (*All About Pancreatic Cancer.* 2005, American Cancer Society). About 32,200 new cases will be detected and about 31,800 deaths due to this disease will occur this year. The prognosis of pancreatic cancer patients under current treatments is poor, and new drugs to treat the disease are needed. The negative prognosis of pancreatic cancer results from the fact that by the time a patient displays symptoms, the cancer has already metastasized. Treatment of pancreatic cancer involves surgery, radiation therapy, chemotherapy or a combination of the three. The current chemotherapy for advanced pancreatic cancer is gemcitabine, a drug that inhibits DNA synthesis. Gemcitabine, while more effective than past treatments, is not sufficient to treat pancreatic cancer as shown by the lethality of this cancer. Furthermore, there is no good therapy to treat pancreatic tumors that become refractory to gemcitabine (Bergenfeldt, M. and Albertsson, M. "Current state of adjuvant therapy in resected pancreatic adenocarcinoma.". *Acta Oncol,* 45: 124-135, 2006). The prognosis of pancreatic cancer patients under current treatments is poor, and new drugs to treat the disease are needed.

Pancreatic cancer cells have high metastatic potentials and exhibit resistance to apoptosis. In pancreatic cancer, constitutive phosphorylation of Raf-MEK-ERK is a common occurrence, and it is a contributive factor to the metastatic potential of the disease by promoting cell dissociation (Tan, X. et al. "Involvement of the mitogen-activated protein kinase kinase 2 in the induction of cell dissociation in pancreatic cancer". *Int J Oncol,* 24: 65-73, 2004). and resistance to apoptosis (Boucher, M. J. et al. "MEK/ERK signaling pathway regulates the expression of Bcl-2, Bcl-X(L), and Mcl-1 and promotes survival of human pancreatic cancer cells". *J Cell Biochem,* 79: 355-369, 2000). Inhibition of this pathway hinders the growth of pancreatic cancer cells (Motomura, W. et al. "Involvement of MEK-ERK signaling pathway in the inhibition of cell growth by troglitazone in human pancreatic cancer cells". *Biochem Biophys Res Commun,* 332: 89-94, 2005). In addition, pancreatic cancer cells also exhibit constitutive activation of NFκB, and its activation correlates with their metastatic potential (Fujioka, S. et al. "Function of nuclear factor kappaB in pancreatic cancer metastasis". *Clin Cancer Res,* 9: 346-354, 2003), and resistance to apoptosis. Finally, the use of a dominant-negative STAT3 vector in pancreatic cancer cell lines significantly decreases their growth rate (Toyonaga, T. et al. "Blockade of constitutively activated Janus kinase/signal transducer and activator of transcription-3 pathway inhibits growth of human pancreatic cancer". *Cancer Lett,* 201: 107-116, 2003), implicating this pathway in the strong metastatic potential exhibited by pancreatic cancer cell lines. Therefore, any potential chemotherapies that can reduce the metastatic potential or re-sensitize pancreatic cancer cells to apoptosis have the potential of being more successful in the treatment of the disease than the currently available ones.

Certain cyclic alkaloid compositions, e.g., manzamines A-F derived from extracts of the marine sponge *Haliclona* sp., have been found to possess useful properties. These compounds have been described in, for example, U.S. Pat. Nos. 4,895,854; 4,895,853; and 4,895,852. Manzamines A-F have the following structures:

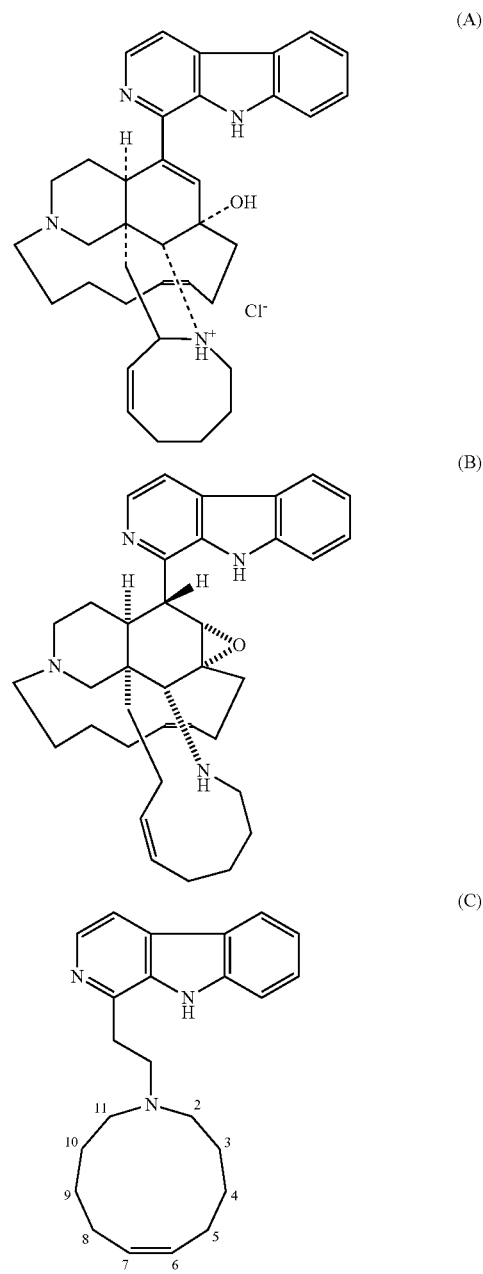

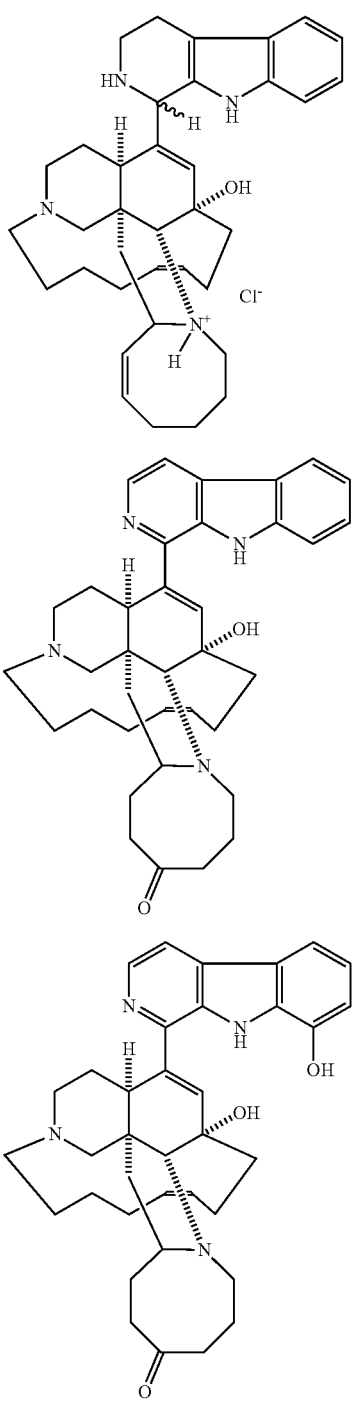

BRIEF SUMMARY

The present invention pertains to the use of manzamine compounds for the treatment of cancer. In a preferred embodiment, a manzamine compound is used as an adjuvant or in combination therapy with existing chemotherapeutics in an anti-cancer therapeutic regimen. Specifically exemplified herein is the use of manzamine A, which has been found to be particularly effective because of its anti-cancer activity and low toxicity.

As described herein, the invention also comprises pharmaceutical compositions, e.g. anti-cancer compositions, containing as an active ingredient an effective amount of one or more manzamine compounds as described herein and a non-toxic, pharmaceutically acceptable carrier or diluent. The pharmaceutical compositions of the subject invention can further comprise other active compounds. As described herein, the invention further comprises novel methods of use of the manzamines, e.g. anti-cancer methods.

In accordance with the subject invention, methods for inhibiting cancer comprise administering to a human or animal in need of such treatment an effective amount of the pharmaceutical compositions described herein. In a preferred embodiment the manzamine compound is used as part of a treatment for pancreatic cancer. In a further preferred embodiment, the manzamine is used in conjunction with a compound that induces apoptosis.

Specifically exemplified herein is the ability of manzamine A to decrease cell disassociation associated with pancreatic cancer cells, its ability to abrogate cell migration which is associated with the metastatic potential of pancreatic cancer cells, and restoration of cancer cell susceptibility to agents, such as TNF-related apoptosis-inducing ligand (TRAIL), that can induce apoptosis. These effects resemble those caused by inhibitors of pMEK.

In accordance with the subject invention, manzamine A has a formerly unrecognized utility in both blocking tumor cell invasion and tumor metastasis as well in restoring cancer cell susceptibility to agents that induce apoptosis and therefore, in one embodiment, has utility as an adjuvant to, or in combination with, existing cancer therapies.

DETAILED DISCLOSURE

Figure 1:
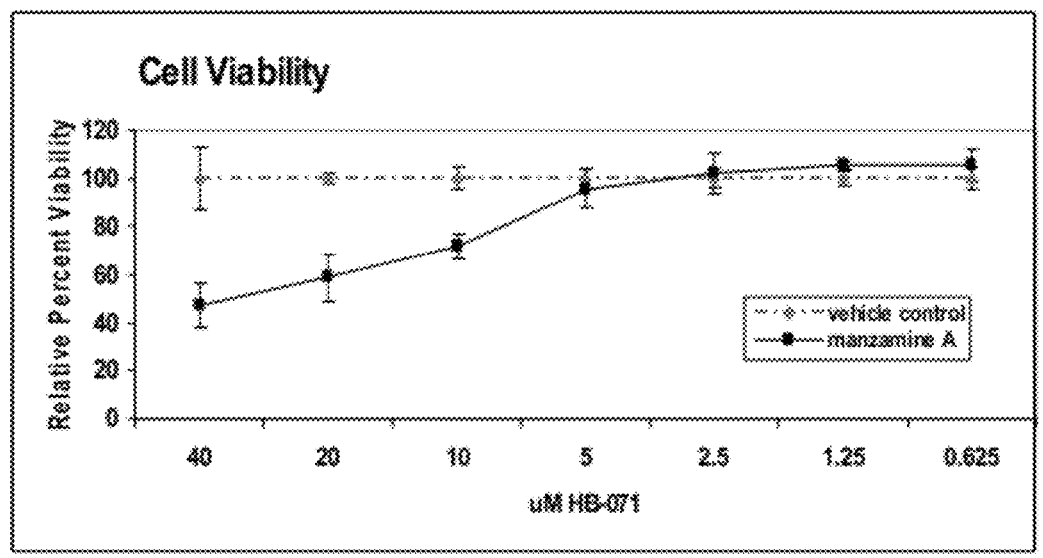
FIG. 1 shows the average of four experiments to determine the cytotoxicity of manzamine A against pancreatic cancer cells.
Figure 2:
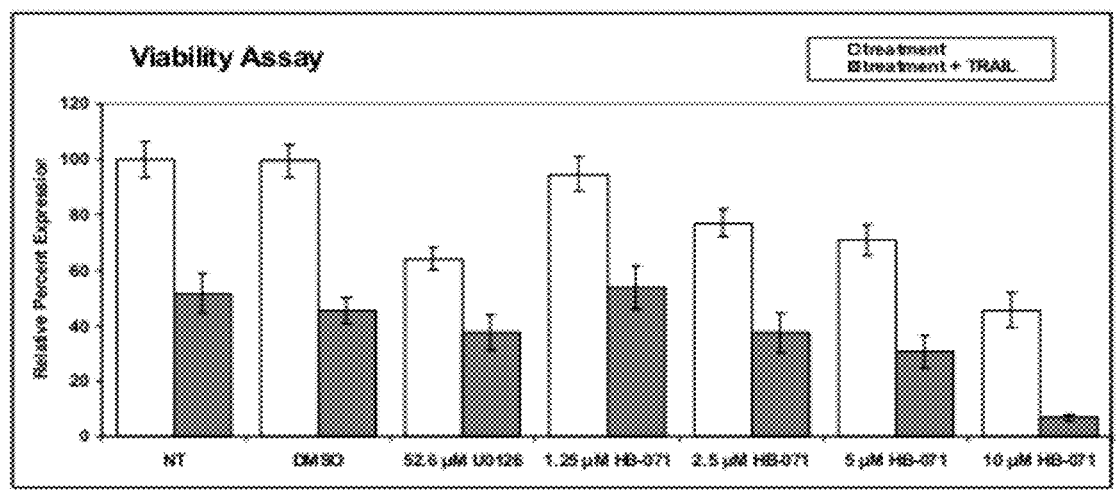
FIG. 2 shows that manzamine A lowers the resistance to apoptosis exhibited by pancreatic cancer cells.
Figure 3:
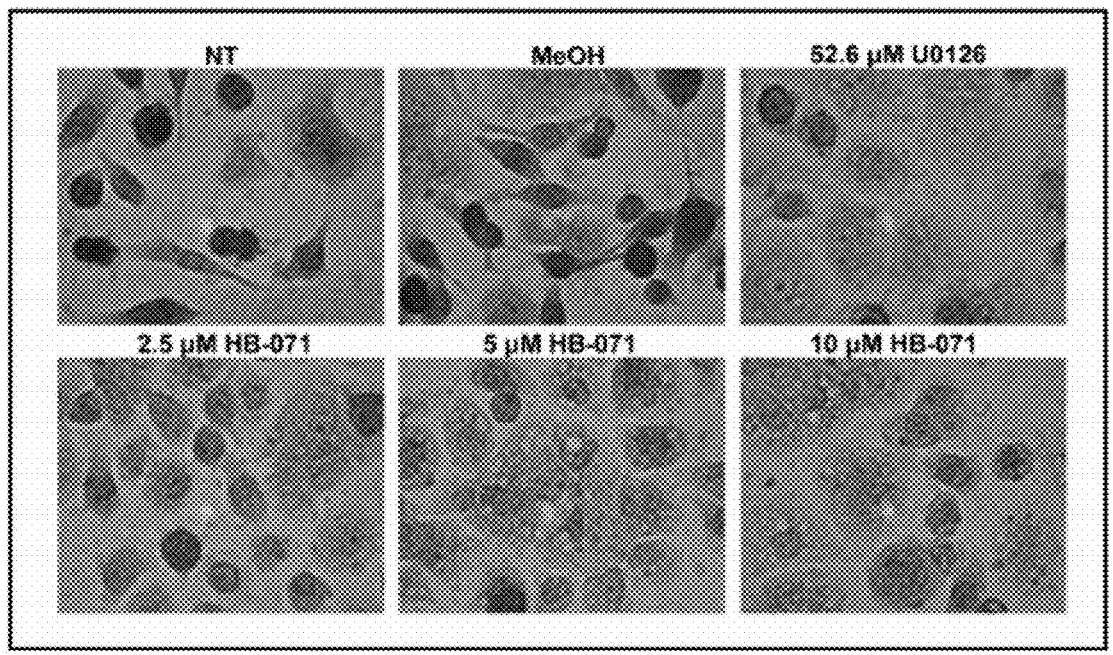
FIG. 3 shows abrogation of cell dissociation by Manzamine A.
Figure 4:
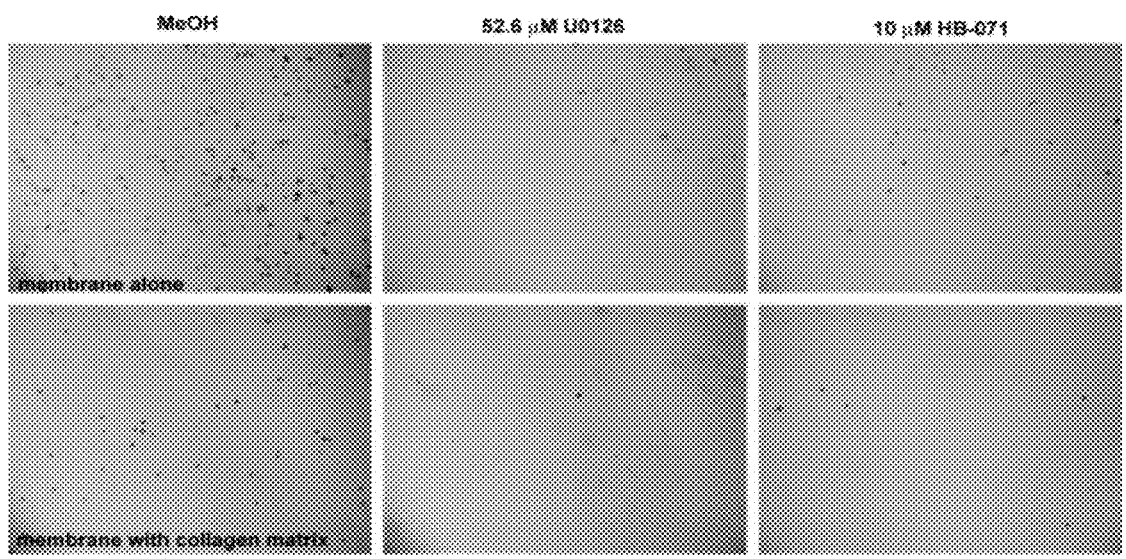
FIG. 4 shows abrogation of cell migration by Manzamine A.

In accordance with the subject invention, methods for inhibiting cancer are provided wherein cancer cells are contacted with an effective amount of a manzamine compound. In a preferred embodiment, a manzamine compound is used as an adjuvant or in combination therapy with existing chemotherapeutics in an anti-cancer therapeutic regimen. Specifically exemplified herein is the use of manzamine A, which has been found to be particularly effective because of its anti-cancer activity and low toxicity.

Thus, the subject invention pertains to novel uses as anti-cancer agents of manzamine compounds and compositions comprising the manzamine compounds. The manzamine compounds of the subject invention can be used to inhibit metastasis of cancer cells and restore sensitivity to programmed cell death.

In one embodiment, the subject invention pertains to the use of compounds having the following General Structure (I):

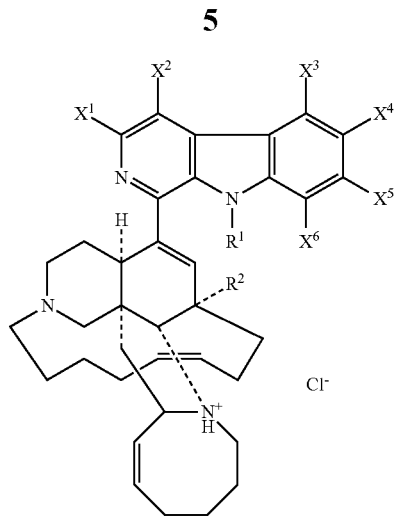

(I)

wherein $X^1$, $X^2$, $X^3$, $X^4$, $X^5$, and $X^6$ are, independently, a hydrogen, halogen, hydroxy, lower alkoxy, lower acyloxy, or lower mono or dialkyl amino group; $R^1$ is hydrogen, lower alkyl, or lower acyl group; $R^2$ is hydrogen, hydroxy, lower alkoxy, or lower acyloxy group.

In a preferred embodiment of the invention, the invention pertains to the cancer chemotherapeutic use as either an adjuvant or in combination therapy of manzamine A having the following structure:

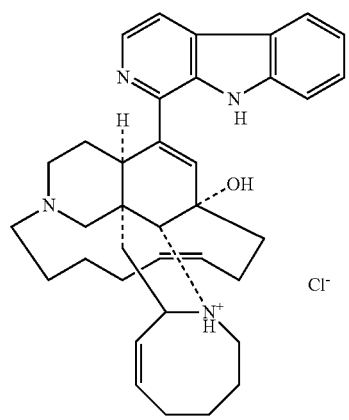

(A)

Further embodiments of the subject invention pertain to the cancer chemotherapeutic use as either an adjuvant or in combination therapy of compounds having General Structures (II)-(IV):

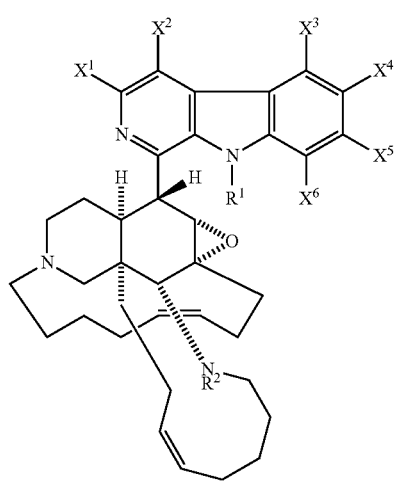

(II)

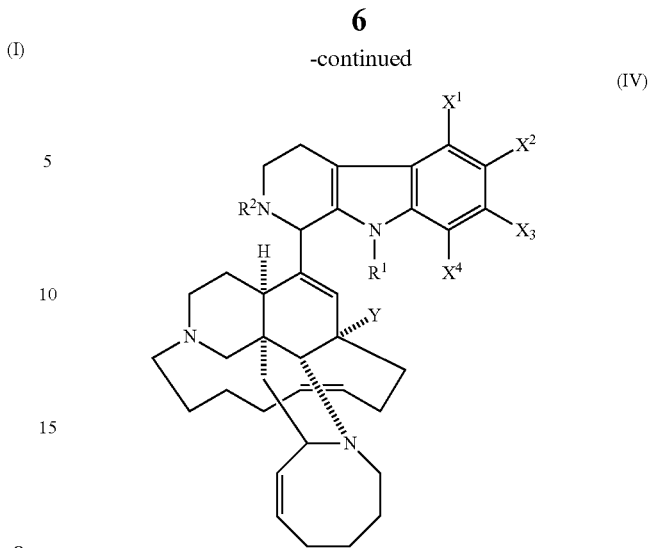

(IV)

wherein $X^1$, $X^2$, $X^3$, $X^4$, $X^5$, and $X^6$ are the same or different and are a hydrogen, halogen, hydroxyl, lower alkoxy, lower acyloxy, thiol, lower alkylthiol, nitro, amino, lower alkylsulfonyl, aminosulfonyl, hydroxy sulfonyl (—SO$_3$H), lower acylamino, lower alkyl, or lower monoalkyl- or dialkylamino group; $R^1$ and $R^2$ are the same or different and are a hydrogen, lower alkyl, or lower acyl group; and Y is a hydrogen, hydroxyl, lower alkoxy, or lower acyloxy group.

In more specific embodiments of the invention, the invention comprises the the cancer chemotherapeutic use as either an adjuvant or in combination therapy of the compounds designated as manzamine B, C, or D of the formulae:

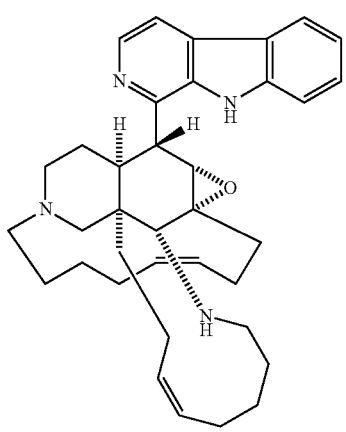

(B)

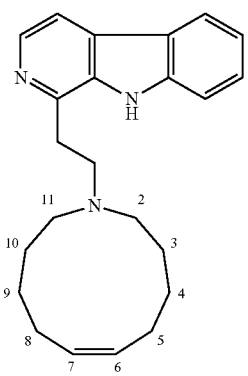

(C)

(D)

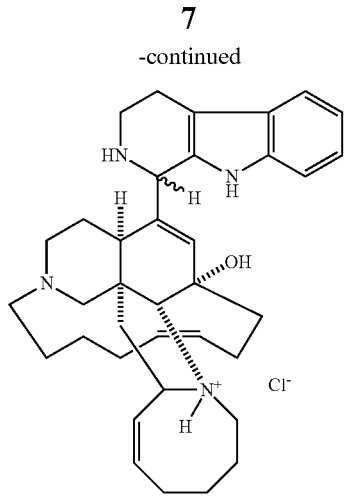

Further embodiments of the subject invention utilize General Structure V:

(V)

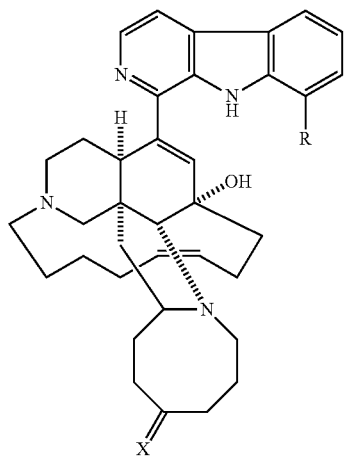

wherein R is a hydrogen, halogen, hydroxy, or lower acyloxy group; and X is a double bonded oxygen, or is the same or different and is any two of a hydrogen, hydroxy, lower alkyl, lower alkoxy, or lower acyloxy group wherein said lower alkyl, alkoxy, or acyloxy groups have preferably, from 1 to 5 carbon atoms.

In one embodiment, the subject invention concerns manzamines E and F which have the following structures:

(E)

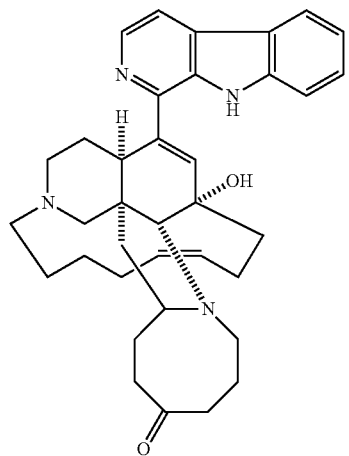

(F)

In other embodiments of the invention, the double bonds in the composition of General Structures (I)-(V) are partially or fully reduced. In further embodiments of the invention, the composition is a mineral acid (e.g., HCl, $H_2SO_4$, $H_3PO_4$, $HNO_3$, etc.) or organic salt of compositions according to the General Structures.

Methods for obtaining these compounds are described in, for example, U.S. Pat. Nos. 4,895,852; 4,895,853; and 4,895,854, which are herein incorporated in their entirety by reference thereto.

Skilled chemists having the benefit of the instant disclosure can readily use procedures to prepare the subject compounds. In carrying out such operations, suitable filtration, chromatographic and other purification techniques can be used. These techniques could include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents such as heptane, ethyl acetate, methylene chloride, methanol, isopropanol, acetonitrile water, trifluoroacetic acid (TFA) and various combinations thereof.

Most preferably, the invention comprises a method for the anti-cancer treatment of a human in need of such treatment, i.e., a human hosting cancer cells, including breast, renal, colon, liver, pancreatic, uterine, or lung tumor cells, or leukemia cells.

In a specific embodiment of the subject invention, manzamine A has been discovered to abrogate cell dissociation as well as the ability of pancreatic cells to migrate through extracellular matrices, both characteristics that correlate with the high metastatic potential of pancreatic cancer cells Furthermore, manzamine A has been shown to abrogate the resistance to TRAIL-mediated apoptosis, which causes the failure of many current therapies. Effects were achieved with manzamine A at a fifth of the dose needed for U0126, a well-characterized MEK inhibitor, to produce similar results. Moreover, unlike U0126 which is fairly unstable in solution, manzamine A is stable and shows little cytotoxicity at small doses. In view of these results, in one embodiment of the subject invention, manzamine A is advantageous for use in combination therapy in the treatment of pancreatic cancer.

All patents, patent applications, provisional applications, and publications referred to or cited herein are incorporated by reference in their entirety, including all figures and tables, to the extent they are not inconsistent with the explicit teachings of this specification.

Materials and Methods

Reagents. Manzamine A was obtained from the Harbor Branch Oceanographic Institute (HBOI) pure compound library. The material was originally isolated from a sponge of the genus *Haliclona* as described in U.S. Pat. No. 4,895,854. The manzamine A stock solution was at 5 mM concentration in methanol. U0126, a known pMEK inhibitor used as a positive control in the assays, was purchased from Calbiochem, San Diego, Calif.

Cell Culture Conditions for the AsPC-1 pancreatic adenocarcinoma cell line. AsPC-1, a pancreatic adenocarcinoma cell line, was obtained from ATCC, grown, aliquotted and frozen stocks were maintained in liquid nitrogen. Aliquots of the stock cells were thawed and grown in RPMI-1640 supplemented with 10% Fetal Bovine Serum, 0.11 mg/ml Sodium Pyruvate, 4.5 g/L D-glucose, 18 mM HEPES Buffer, 100 U/ml penicillin G sodium, 100 μg/ml streptomycin sulfate, 0.25 μg/ml amphotericin B, 2 mM L-glutamine and 50 μg/ml gentamicin (Complete RPMI). Cells were maintained in a humidified incubator at 37° C. and 5% $CO_2$.

Cell viability assays. A 3-[4,5-Dimethyl-2-thiazolyl]-2,5-diphenyl-2H-tetrazolium bromide (MTT) based assay was used to determine cell viability. For the MTT assay, 12,000 AsPC-1 cells were plated into a 96-well tissue culture plate at a volume of 200 μl/well. Cells were allowed to adhere for 24 hours. At the end of this incubation, 100 μl of medium were removed from each test well and 100 μl of medium containing treatment were added. Treatment consisted of 5 μM or 50 μM of Manzamine A, media alone, media with methanol, or 20 μg/ml U0126. The cells were then incubated for 48 hours at 37° C. and 5% $CO_2$. After this incubation, 75 μl 5 mg/ml MTT were added to each well. The cells were then incubated for 3 hours at 37° C. The plates were centrifuged for 10 minutes at 800 rpm. The supernatant was removed and 200 μl acidified isopropyl alcohol (1:500 solution of hydrochloric acid to isopropanol) was added to each well. The plates were shaken for 15 minutes. The absorbencies of these solutions were measured at 570 nm with a plate reader (NOVOstar, BMG Labtech Inc., Durham, N.C.). The resulting absorbencies were plotted using Microsoft Excel.

TRAIL induced apoptosis. 12,000 AsPC-1 cells were plated on a 96-well tissue culture plate at a volume of 200 μl/well, allowing for twelve replicate wells per treatment. Cells were allowed to adhere for 24 hours. At the end of this incubation, 100 μl of medium were removed from each test well and 100 μl of medium containing treatment were added. Treatment consisted of media alone, media with methanol, 10 μM Manzamine A or 20 μg/ml U0126. The cells were then incubated for 48 hours at 37° C. and 5% $CO_2$. After this incubation, half of the wells of each treatment were incubated with 100 ng/ml Super Killer TRAIL (Alexis, San Diego, Calif.) for 18 hours at 37° C. and 5% $CO_2$. At the end of this incubation, 75 μl of a 5 mg/ml MTT solution were added to each well. The cells were then incubated for 3 hours at 37° C. The plates were centrifuged for 10 minutes at 800 rpm. The supernatant was removed and 200 μl acidified isopropyl alcohol (1:500 solution of hydrochloric acid to isopropanol) were added to each well. The plates were shaken for 15 minutes. The absorbencies of these solutions were measured at 570 nm with a plate reader (NOVOstar, BMG Labtech Inc., Durham, N.C.). The resulting absorbencies were plotted using Microsoft Excel.

In Vitro Cell Invasion Assay. The invasiveness of AsPC-1 cells alone, treated with our test compounds or treated with U0126 as a positive control will be evaluated in 24-well transwell chambers, as described by Fu et al. "Effects of raf kinase inhibitor protein expression on suppression of prostate cancer metastasis". *J Natl Cancer Inst*, 95: 878-889, 2003. Briefly, the upper and lower culture compartments of each well are separated by polycarbonate membranes (8-μm pore size). To determine baseline migration, $2.5 \times 10^4$ cells in 0.5 mL of complete medium containing 5% FBS are placed into the upper compartment of uncoated wells (BD Discovery Labware, San Diego, Calif.), and 0.75 mL of complete medium containing 10% FBS are placed into the lower compartment. In parallel, to assess the ability of the same cells to penetrate a collagen matrix, the experiment is repeated using upper compartments coated with 100 μg/cm² of collagen matrix (BD Discovery Labware, San Diego, Calif.). The transwell chambers are incubated for 24 hours at 37 ° C. in 95% air and 5% $CO_2$. Cell penetration through the membrane is detected by staining the cells on the porous membrane with a Diff-Quik stain kit' observing under the microscopic and capturing images with a digital camera.

Statistical Analysis of Results. Statistical analysis of the data sets to determine mean, standard deviation, and standard error of the mean was performed using Microsoft Excel. Data sets were compared using the Student's T Test. A p value≤0.05 was considered significant. Outliers were detected through the Grubbs Test.

The scope of the invention is not limited by the specific examples and suggested procedures and uses related herein since modifications can be made within such scope from the information provided by this specification to those skilled in the art.

The examples which follow are not meant to be fully inclusive of all forms of cancer which can be treated with manzamine A nor is it inclusive of all chemotherapeutic agents with which manzamine A could be used in combination for the treatment of cancer.

EXAMPLE 1

Measurement of Morphological Changes Induced in AsPC-1 Cells by Manzamine A

The high metastatic potential exhibited by pancreatic cancer cells is in part due to their ability to dissociate from other pancreatic cells and grow in single cell formation. An observation was made that inhibiting the constitutive activation of MEK abrogates cell dissociation (Tan, X. et al., 2004 "Involvement of the mitogen-activated protein kinase kinase 2 in the induction of cell dissociation in pancreatic cancer" *Int J Oncol* 24(1):65-73), a precursor step in metastasis. Therefore, to determine if manzamine A caused the abrogation of cell dissociation, AsPC-1 cells were treated for 48 hours with media alone, media containing methanol, 52.6 μM U0126 or 1.25, 2.5, 5, 10 μM Manzamine A. At the end of this incubation, cells were visualized with the microscope and photographed with a digital camera. Manzamine A caused abrogation of cell dissociation similar to that caused by pMEK inhibitors.

The abrogation was stronger at the 5 and 10 μM dose of Manzamine A. Thus, in one embodiment, the cancers that can be treated in accordance with the subject invention are those for which inhibition of phosphorylated mitogen-activated protein kinase kinase 2 (p-MEK) causes the cancer to be less likely to proliferate and/or metastasize, and/or which either directly or indirectly makes the cancer cells more prone to apoptosis (all of which are collectively referred to herein as "inhibiting the growth" of cancer cells).

EXAMPLE 2

Measurement of the Ability of AsPC-1 Cells to Migrate Through a Matrix

Another contributor to the high metastatic potential of pancreatic cancer cells is their ability to migrate through extracellular matrices, which normal cells are unable to do. To determine if manzamine A prevented cell migration, AsPC-1 cells were treated for 48 hours with media alone, media containing methanol, 52.6 μM U0126 or 1.25, 2.5, 5, 10 μM Manzamine A and subjected to an in vitro cell invasion assay as described in the materials and methods. At the end of this incubation, cells were stained, visualized with the microscope and photographed with a digital camera. Manzamine A at doses of 5 and 10 μM prevented cell migration similar to that caused by the pMEK inhibitor U0126.

EXAMPLE 3

Measurement of Sensitivity of AsPC-1 Cells to TRAIL-induced Apoptosis when Treated with Manzamine A To determine if treatment with manzamine A sensitized pancreatic cancer cells to TRAIL-mediated apoptosis, cells were treated with media alone, media containing methanol, 52.6 μM U0126, and 10 μM Manzamine A for 48 hours as per the protocol listed in the materials and methods. At the end of this treatment, half of the cells were further treated with 100 mg/ml super killer TRAIL. Treatment with 10 μM manzamine A or the inhibitor U0126 induced some cytotoxicity. Treatment with super killer TRAIL induced some apoptosis in all the cells regardless of treatment. However, when the cells were treated with super killer TRAIL antibody in addition to the inhibitors, pre-treatment with manzamine A caused the greatest level of TRAIL-mediated cytotoxicity.

EXAMPLE 4

Formulation and Administration

The compounds of the invention are useful for various non-therapeutic and therapeutic purposes. It is apparent from the testing that the compounds of the invention are effective for decreasing metastatic potential and resistance to apoptosis similar to known pMEK inhibitors. Because of the properties of the compounds, they are useful to prevent unwanted cell growth in a wide variety of settings including in vitro uses. As disclosed herein, they are also useful for treating cancer cells in animals and humans.

Therapeutic application of the compounds and compositions containing them can be accomplished by any suitable therapeutic method and technique presently or prospectively known to those skilled in the art.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application.

We claim:
1. A method for inducing apoptosis in pancreatic cancer cells wherein said method comprises administering, to the cancer cells, an effective amount of manzamine A and TNF-related apoptosis-inducing ligand.

* * * * *